(12) United States Patent
Yoshimi et al.

(10) Patent No.: US 7,410,649 B2
(45) Date of Patent: Aug. 12, 2008

(54) PERSONAL CARE COMPOSITIONS COMPRISING VISIBLE BEADS, CATIONIC POLYMER, AND SURFACTANT

(75) Inventors: Naohisa Yoshimi, Nishinomiya (JP); Hideki Miyamoto, Nishinomiya (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/248,069

(22) Filed: Oct. 12, 2005

(65) Prior Publication Data

US 2006/0083761 A1    Apr. 20, 2006

Related U.S. Application Data

(60) Provisional application No. 60/619,214, filed on Oct. 15, 2004.

(51) Int. Cl.
*A61K 8/02* (2006.01)
*A61K 9/14* (2006.01)

(52) U.S. Cl. .................. 424/401; 424/489; 514/846
(58) Field of Classification Search ................. 424/401, 424/489; 514/846
See application file for complete search history.

(56) References Cited

U.S. PATENT DOCUMENTS

| | | | |
|---|---|---|---|
| 6,045,813 A | 4/2000 | Ferguson et al. | |
| 6,534,091 B1 | 3/2003 | Garces Garces et al. | |
| 6,797,683 B2 | 9/2004 | Shana'a et al. | |
| 2002/0012645 A1* | 1/2002 | Midha et al. | 424/70.2 |
| 2003/0165454 A1 | 9/2003 | Snyder et al. | |
| 2003/0171230 A1 | 9/2003 | Shana'a et al. | |
| 2004/0047822 A1 | 3/2004 | Zamudo-Tena et al. | |

FOREIGN PATENT DOCUMENTS

| | | | |
|---|---|---|---|
| WO | WO 97/23194 | * | 7/1997 |
| WO | WO 97/23194 A1 | | 7/1997 |
| WO | WO 00/06089 | * | 2/2000 |
| WO | WO 00/06089 A1 | | 2/2000 |
| WO | WO 00/06090 A1 | | 2/2000 |
| WO | WO 00/40207 A1 | | 7/2000 |
| WO | WO 00/40212 A1 | | 7/2000 |

* cited by examiner

*Primary Examiner*—Johann Richter
*Assistant Examiner*—Konata M George
(74) *Attorney, Agent, or Firm*—Jason J. Camp; Bridget Murray

(57) ABSTRACT

Personal care compositions comprise visible beads, cationic polymer, and surfactant. The visible beads in the personal care compositions can be utilized to provide an aesthetically pleasing appearance to the product. The visible beads can also be utilized to encapsulate and deliver skin benefit agents to the skin or hair. The visible beads can also encapsulate materials that are otherwise incompatible with the personal care composition matrix to preserve product stability.

15 Claims, No Drawings

PERSONAL CARE COMPOSITIONS COMPRISING VISIBLE BEADS, CATIONIC POLYMER, AND SURFACTANT

CROSS-REFERENCE TO RELATED APPLICATION(S)

This application claims the benefit of Provisional Application Ser. No. 60/619,214, filed Oct. 15, 2004.

FIELD OF THE INVENTION

The present invention relates to personal care compositions comprising visible beads and cationic polymer. The compositions are suitable for cleansing and/or conditioning the skin and/or the hair and which may be used, for example, in the form of foam bath preparations, shower products, skin cleansers, skin moisturizers, hair shampoos, hair conditioners, and the like.

BACKGROUND OF THE INVENTION

Personal care compositions that are suitable for cleansing and/or conditioning the skin and/or hair come in many different product forms. One popular form of personal care compositions is a liquid body wash product. Consumer preferred liquid body wash products exhibit good cleaning performance and good lathering performance, yet are mild to the skin and deposit skin benefit agents to the skin to provide a variety of benefits to the consumer. Consumers also prefer a product that is aesthetically pleasing, as displayed in a store and as stored in a shower or bath.

There has thus been a desire to develop a personal care composition that is mild to the skin and/or hair, has an aesthetically pleasing appearance, is able to deliver skin benefit agents to the skin and/or hair, and is stable.

SUMMARY OF THE INVENTION

The personal care compositions of the present invention comprise visible beads, cationic polymer, and surfactant. The visible beads in the present compositions can be utilized to provide an aesthetically pleasing appearance to the product. The visible beads can also be utilized to encapsulate and deliver skin benefit agents to the skin or hair. The visible beads can also encapsulate materials that are otherwise incompatible with the personal care composition matrix to preserve product stability.

The visible beads preferably comprise a structural material comprising lactose, cellulose and hydroxypropyl methylcellulose. The structural material of the visible beads can further comprise a pigment to impart a colored appearance to the visible beads. The visible beads can further comprise an encompassed material, such as a skin benefit agent. The personal care compositions preferably have a viscosity of from about 1,000 to less than about 40,000 centipoise. The cationic polymer utilized in the present compositions is preferably guar hydroxypropyl trimonium chloride. The compositions preferably further comprise a high molecular weight ester oil. Preferred high molecular weight ester oils include poly alpha-olefins, such as polydecene.

The present invention further relates to methods of using the personal care compositions described herein to cleanse and/or moisturize skin and/or hair.

DETAILED DESCRIPTION OF THE INVENTION

Visible Beads

The compositions of the present invention comprise visible beads. A visible bead is a particle which can be distinctively detected as an individual particle by the naked eye when comprised in the present composition, and which is stable in the present composition. The visible bead can be of any size, shape, or color, according to the desired characteristic of the product, so long as it is distinctively detected as an individual particle by the naked eye. The visible beads will typically have the shape of a small round ball. Generally, a visible bead has an average diameter of from about 50 μm to about 5000 μm, preferably from about 100 μm to about 3000 μm, more preferably from about 300 μm to about 1000 μm. By stable, it is meant that the visible beads are not disintegrated, agglomerated, or separated under normal shelf conditions.

The visible beads herein are typically incorporated in the present compositions at levels of from about 0.01% to about 25%, preferably from about 0.01% to about 5%, and more preferably from about 0.05% to about 3%, by weight of the composition.

The visible bead herein will typically comprise a structural material and preferably an encompassed material.

The structural material provides a certain strength to the visible beads so that they retain their distinctively detectable structure in the present composition under normal shelf conditions. In one embodiment, the structural material further can be broken and disintegrated with very little shear on the hand with the fingers upon use.

The visible beads can be solid or liquid, filled or un-filled, as long as they are stable in the present composition. The structural material used for making the visible beads varies depending on the compatibility with other components, as well as material, if any, to be encompassed in the visible beads. Exemplary materials for making the visible beads herein include: polysaccharide and saccharide derivatives such as crystalline cellulose, cellulose acetate, cellulose acetate butyrate, cellulose acetate phthalate, cellulose nitrate, ethylcellulose, hydroxypropylcellulose, hydroxypropylmethylcellulose, hydroxypropylmethylcellulose phthalate, methyl cellulose, sodium carboxymethylcellulose, gum acacia (gum arabic), agar, agarose, maltodextrin, sodium alginate, calcium alginate, dextran, starch, galactose, glucosamine, cyclodextrin, chitin, amylose, amylopectin, glycogen, laminaran, lichenan, curdlan, inulin, levan, pectin, mannan, xylan, alginic acid, arabic acid, glucommannan, agarose, agaropectin, prophyran, carrageenen, fucoidan, glycosaminoglycan, hyaluronic acid, chondroitin, peptidoglycan, lipopolysaccharide, guar gum, starch, and starch derivatives; oligosaccharides such as sucrose, lactose, maltose, uronic acid, muramic acid, cellobiose, isomaltose, planteose, melezitose, gentianose, maltotriose, stachyose, glucoside and polyglucoside; monosaccharides such as glucose, fructose, and mannose; synthetic polymers such as acrylic polymers and copolymers including polyacrylamide, poly(alkyl cyanoacrylate), and poly(ethylene-vinyl acetate), and carboxyvinyl polymer, polyamide, poly(methyl vinyl ether-maleic anhydride), poly(adipyl-L-lysine), polycarbonate, polyterephthalamide, polyvinyl acetate phthalate, poly (terephthaloyl-L-lysine), polyarylsulfone, poly (methylmethacrylate), poly(ε-caprolactone), polyvinylpyrrolidone, polydimethylsiloxane, polyoxyethylene, polyester, polyglycolic acid, polylactic acid, polyglutamic acid, polylysine, polystyrene, poly(styrene-acrylonitrile), polyimide, and poly(vinyl alcohol); and other material such as fat, fatty acid, fatty alcohol, milk solids, molasses, gelatin, gluten, albumin, shellac, caseinate, bees wax, carnauba wax, spermaceti wax, hydrogenated tallow, glycerol monopalmitate, glycerol dipalmitate, hydrogenated castor oil, glycerol monostearate, glycerol distearate, glycerol tristearate, 12-hydroxystearyl alcohol, protein, and protein derivatives; and mixtures thereof. Components herein may be described in other sections as useful components for the present composition. The components herein, however, are substantially used to make the structure of the visible beads, and are not dissolved or dispersed in the bulk of the present composition under normal shelf conditions.

Highly preferable structural material herein comprises components selected from the group consisting of polysaccharides and their derivatives, saccharides and their derivatives, oligosaccharides, monosaccharides, and mixtures thereof, still preferably, components from the above mentioned group wherein components having various water solubility are selected. In a particularly preferred embodiment, the structural material comprises lactose, cellulose, and hydroxypropyl methylcellulose.

Suitable visible beads also include organogel particles as described in detail in U.S. Pat. No. 6,797,683. Visible beads that are organogel particles typically comprise a structural material selected from poloxamer compounds (i.e. polyoxypropylene-polyoxyethylene block copolymer such as Pluronic F-127 available from BASF), waxes (e.g., beeswax, paraffin, water-insoluble wax, carbon-based wax, silicone wax, microcrystalline wax, etc.), triglycerides, acid triglycerides, polymers, fluoroalkyl (meth)acrylate polymers and copolymers, acrylate polymers, ethylene/acrylate copolymers, polyethylene, polypropylene polymers and copolymers, fatty acids, fatty alcohols, fatty acid esters, fatty acid ethers, fatty acid amides, alkylene polyhydric alcohols, fatty acid amide of an alkanolamine, glyceryl monostearate, (aryl-substituted)sugars, dibenzyl sorbitol (or mannitoal, rabbitol, etc.), condensates and precondensates of lower monohydric alcohols, trihydroic alcohols, lower polyglycols, propylene/ethylene polycondensates, and the like. Preferred structural material for visible beads that are organogel particles include beeswax, carnauba wax, low molecular weight ethylene homopolymers (e.g. Polywax 500, Polywax 1000, or Polywax 2000 polyethylene materials available from Baker Petrolite Corp.), or paraffin wax.

The visible beads herein may encompass, contain, or be filled with an encompassed material. Such encompassed material can be water soluble or water insoluble. Suitable encompassed materials include skin benefit agents as described herein such as: vitamins, amino acids, proteins and protein derivatives, herbal extracts, pigments, dyes, antimicrobial agents, chelating agents, UV absorbers, optical brighteners, silicone compounds, perfumes, humectants, and mixtures thereof. In one embodiment, water soluble components are preferred encompassed material. The encompassed materials herein are substantially retained within the visible beads, and are substantially not dissolved in the bulk of the present composition under normal shelf conditions.

Particularly useful commercially available visible beads herein are those with tradenames Unisphere and Unicerin available from Induchem AG (Switzerland), and Confetti Dermal Essentials available from United-Guardian Inc. (NY, USA). Unisphere and Unicerin particles are made of microcrystalline cellulose, hydroxypropyl cellulose, lactose, vitamins, pigments, and proteins. Upon use, the Unisphere and Unicerin particles can be disintegrated with very little shear on the hand with the fingers with practically no resistance, and readily dissolve in the composition.

Suitable visible beads for incorporation in the present compositions are described in detail in U.S. Pat. No. 6,797,683 (organogel particles); U.S. Pat. No. 6,045,813 (rupturable beads); U.S. 2004/0047822 A1 (visible capsules); and WO 97/23194 (capsulated or particulated oily substances).

Cationic Polymer

The personal care compositions according to the present invention comprise a cationic polymer. Cationic polymers can be useful in the compositions of the present invention to provide desirable skin feel attributes, such as skin conditioning. Also, the addition of a cationic polymer can be advantageous in combination with the visible beads or water-insoluble oils for providing enhanced deposition of the visible beads or water-insoluble oils. The cationic polymer is preferably present at a level from about 0.01% to about 5%, preferably from about 0.01% to about 3% and especially from about 0.01% to about 2% by weight.

Suitable cationic polymers include high molecular weight materials (mass-average molecular weight determined, for instance, by light scattering, being generally from about 2,000 to about 5,000,000, preferably from about 5,000 to about 3,000,000 more preferably from 100,000 to about 1,000,000).

Representative classes of cationic polymers suitable herein include cationic guar gums, cationic polysaccharides; cationic homopolymers and copolymers derived from acrylic and/or methacrylic acid; cationic cellulose resins, quaternized hydroxy ethyl cellulose ethers; cationic copolymers of dimethyldiallylammonium chloride and acrylamide and/or acrylic acid; cationic homopolymers of dimethyldiallylammonium chloride; copolymers of dimethyl aminoethylmethacrylate and acrylamide, acrylic acid/dimethyldiallylammonium chloride/acrylamide copolymers, quaternised vinyl pyrrolidone acrylate or methacrylate copolymers of amino alcohol, quaternized copolymers of vinyl pyrrolidone and dimethylaminoethylmethacrylamide, vinyl pyrollidone/vinyl imidazolium methochloride copolymers and polyalkylene and ethoxypolyalkylene imines; quaternized silicones, terpolymers of acrylic acid, methacrylamidopropyl trimethyl ammonium chloride and methyl acrylate, and mixtures thereof.

By way of non-limiting exemplification, cationic polymers suitable for use herein include cationic guar gums such as hydroxypropyl trimethyl ammonium guar gum (d.s. of from 0.11 to 0.22) available commercially under the trade names Jaguar C-14-S(RTM) and Jaguar C-17(RTM) and also Jaguar C-16(RTM), which contains hydroxypropyl substituents (d.s. of from 0.8-1.1) in addition to the above-specified cationic groups, and quaternized hydroxy ethyl cellulose ethers available commercially under the trade names Ucare Polymer JR-30M, JR-400, LR400, Catanal (RTM) and Celquat. Other suitable cationic polymers are homopolymers of dimethyldiallylammonium chloride available commercially under the trade name Merquat 100, copolymers of dimethyl aminoethylmethacrylate and acrylamide, copolymers of dimethyldiallylammonium chloride and acrylamide, available commercially under the trade names Merquat 550 and Merquat S, acrylic acid/dimethyldiallylammonium chloride/acrylamide copolymers available under the trade name Merquat 3330, terpolymers of acrylic acid, methacrylamidopropyl trimethyl ammonium chloride and methyl acrylate commercially available under the tradename Merquat 2001, quaternized vinyl pyrrolidone acrylate or methacrylate copolymers of amino alcohol available commercially under the trade name Gafquat, for example Polyquaternium 11, 23 and 28 (quaternized copolymers of vinyl pyrrolidone and dimethyl aminoethylmethacrylate—Gafquat 755N and quaternized copolymers of vinyl pyrrolidone and dimethyl aminoethylmethacrylamide—HS-100), vinyl pyrrolidone/vinyl imidazolium methochloride copolymers available under the trade names Luviquat FC370, Polyquaternium 2, and polyalkyleneimines such as polyethylenimine and ethoxylated polyethylenimine. Also suitable for use herein are those cationic polymers commercially available under the tradename N-Hance from Aqualon.

Surfactants

The present compositions comprise surfactants, preferably to provide a skin and/or hair cleansing benefit. The surfactants used herein are preferably water-soluble surfactants. Water-soluble, as defined herein, means a surfactant having a molecular weight of less than about 20,000 wherein the surfactant is capable of forming a clear isotropic solution when dissolved in water at 0.2% w/w under ambient conditions. Surfactants suitable for inclusion in compositions according to the present invention generally have a lipophilic chain length of from about 6 to about 22 carbon atoms and can be selected from anionic, nonionic, zwitterionic and amphoteric surfactants and mixtures thereof. The total level of surfactant in the present compositions is preferably from about 2% to about 40%, more preferably from about 3% to about 25% by weight, and especially from about 5% to about 20%, by weight of the composition. The compositions preferably comprise a mixture of anionic with zwitterionic and/or amphoteric surfactants. The weight ratio of anionic surfactant: zwitterionic and/or amphoteric surfactant is in the range from about 1:10 to about 10:1, preferably from about 1:5 to about 5:1, more preferably from about 1:3 to about 3:1. Other suitable compositions within the scope of the invention comprise mixtures of anionic, zwitterionic and/or amphoteric surfactants with one or more nonionic surfactants.

The compositions of the invention can comprise a water-soluble anionic surfactant at levels from about 0.1% to about 25%, more preferably from about 1% to about 20%, and especially from about 5% to about 15% by weight.

Water soluble anionic surfactants suitable for inclusion in the compositions of the invention include alkyl sulfates, ethoxylated alkyl sulfates, alkyl ethoxy carboxylates, alkyl glyceryl ether sulfonates, ethoxy ether sulfonates, methyl acyl taurates, fatty acyl glycinates, N-acyl glutamates, acyl isethionates, alkyl sulfosuccinates, alkyl ethoxysulphosuccinates, alpha-sulfonated fatty acids, their salts and/or their esters, alkyl phosphate esters, ethoxylated alkyl phosphate esters, acyl sarcosinates and fatty acid/protein condensates, soaps such as ammonium, magnesium, potassium, triethanolamine and sodium salts of lauric acid, myristic acid and palmitic acid, acyl aspartates, alkoxy cocamide carboxylates, (ethoxylated) alkanolamide sulphosuccinates, ethoxylated alkyl citrate sulphosuccinates, acyl ethylene diamine triacetates, acylhydroxyethyl isethionates, acyl amide alkoxy sulfates, linear alkyl benzene sulfonates, paraffin sulfonates, alpha olefin sulfonates, alkyl alkyoxy sulfates, and mixtures thereof. Alkyl and/or acyl chain lengths for these surfactants are $C_6$-$C_{22}$, preferably $C_{12}$-$C_{18}$ more preferably $C_{12}$-$C_{14}$.

Additional water-soluble anionic surfactants suitable for use in the compositions according to the present invention are the salts of sulfuric acid esters of the reaction product of 1 mole of a higher fatty alcohol and from about 1 to about 12 moles of ethylene oxide, with sodium, ammonium and magnesium being the preferred counterions. Particularly preferred are the alkyl ethoxy sulfates containing from about 2 to 6, preferably 2 to 4 moles of ethylene oxide, such as sodium laureth-2 sulfate, sodium laureth-3 sulfate, ammonium laureth-3 sulfate and magnesium sodium laureth-3.6 sulfate. In preferred embodiments, the anionic surfactant contains at least about 50% especially at least about 75% by weight of ethoxylated alkyl sulfate.

In addition to the broad range ethoxylated alkyl sulfates obtained via conventional sodium catalysed ethoxylation techniques and subsequent sulphation processes, ethoxylated alkyl sulfates obtained from narrow range ethoxylates (NREs) are also suitable water-soluble anionic surfactants for use in the present compositions. Narrow range ethoxylated alkyl sulfates suitable for use herein are selected from sulphated alkyl ethoxylates containing on average from about 1 to about 6, preferably from about 2 to about 4 and especially about 3 moles of ethylene oxide such as NRE sodium laureth-3 sulfate. NRE materials suitable for use herein contain distributions of the desired ethylene oxide ($EO_n$) in the ranges of from 15% to about 30% by weight of $EO_n$, from about 10% to about 20% by weight of $EO_{n+1}$ and from about 10% to about 20% by weight of $EO_{n-1}$. Highly preferred NRE materials contain less than about 9% by weight of ethoxylated alkyl sulfate having 7 or more moles of ethylene oxide and less than about 13% by weight of non-ethoxylated alkyl sulfate. Suitable laureth 3 sulfate NRE materials are available from Hoechst under the trade names GENAPOL ZRO Narrow Range and GENAPOL Narrow Range.

The compositions of the present invention may contain, as a water-soluble anionic surfactant alkyl ethoxy carboxylate surfactant at a level of from about 0.5% to about 15%, preferably from about 1% to about 10%, more preferably from about 1% to about 6% and especially from about 1% to about 4% by weight. Alkyl ethoxy carboxylate surfactant is particularly valuable in the compositions according to the present invention for the delivery of excellent skin mildness attributes in combination with excellent rinsing performance and desirable lather characteristics.

Alkyl ethoxy carboxylates suitable for use herein have the general formula (I):

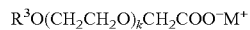

$$R^3O(CH_2CH_2O)_kCH_2COO^-M^+$$

wherein $R^3$ is a $C_{10}$ to $C_{16}$ alkyl or alkenyl group, preferably a $C_{11}$-$C_{15}$, more preferably a $C_{12}$-$C_{14}$ alkyl or $C_{12}$-$C_{13}$ alkyl group, k is an average value of ethoxylation ranging from 2 to about 7, preferably from about 3 to about 6, more preferably from about 3.5 to about 5.5, especially from about 4 to about 5, most preferably from about 4 to about 4.5, and M is a water-solubilizing cation, preferably an alkali metal, alkaline earth metal, ammonium, lower alkanol ammonium, and mono-, di-, and tri-ethanol ammonium, more preferably sodium, potassium and ammonium, most preferably sodium and ammonium and mixtures thereof with magnesium and calcium ions.

Particularly preferred as water-soluble anionic surfactants suitable for use herein are alkyl ethoxy carboxylate surfactants having a selected distribution of alkyl chain length and/or ethoxylate. Thus, the alkyl ethoxy carboxylate surfactants suitable for use in the compositions according to the present invention may comprise a distribution of alkyl ethoxy carboxylates having different average values of $R^3$ and/or k.

The average value of k will generally fall in the range of from about 3 to about 6 when the average $R^3$ is $C_{11}$, $C_{12}$, $C_{13}$ or $C_{14}$. Preferred water-soluble anionic alkyl ethoxy carboxylate surfactants suitable for use herein are the $C_{12}$ to $C_{14}$ (average EO 3-6) ethoxy carboxylates and the $C_{12}$ to $C_{13}$ (average EO 3-6) ethoxy carboxylates. Suitable materials include salts of NEODOX 23-4 (RTM) available from Shell Inc. (Houston, Tex., USA) and EMPICOL (RTM) CBCS (Albright & Wilson). Highly preferred for use herein are alkyl ethoxy carboxylate surfactants wherein, when $R^3$ is a $C_{12}$-$C_{14}$ or $C_{12}$-$C_{13}$ alkyl group and the average value of k is in the range of from about 3 to about 6, more preferably from about 3.5 to about 5.5, especially from about 4 to about 5 and most preferably from about 4 to about 4.5.

In preferred embodiments the compositions are substantially free of soap, i.e. they contain less than about 5%, preferably less than about 1%, preferably 0%, by weight, of soap.

The compositions according to the present invention may additionally comprise water-soluble nonionic surfactant at levels from about 0.1% to about 20%, more preferably from about 0.1% to about 10%, and especially from about 1% to about 8% by weight. Surfactants of this class include sucrose polyester surfactants, $C_{10}$-$C_{18}$ alkyl polyglycosides and polyhydroxy fatty acid amide surfactants having the general formula (III):

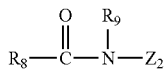

The preferred N-alkyl, N-alkoxy or N-aryloxy, polyhydroxy fatty acid amide surfactants according to formula (III) are those in which $R_8$ is $C_5$-$C_{31}$ hydrocarbyl, preferably $C_6$-$C_{19}$ hydrocarbyl, including straight-chain and branched chain alkyl and alkenyl, or mixtures thereof and $R_9$ is typically, hydrogen, $C_1$-$C_8$ alkyl or hydroxyalkyl, preferably methyl, or a group of formula —$R^1$—O—$R^2$ wherein $R^1$ is $C_2$-$C_8$ hydrocarbyl including straight-chain, branched-chain and cyclic (including aryl), and is preferably $C_2$-$C_4$ alkylene, $R^2$ is $C_1$-$C_8$ straight-chain, branched-chain and cyclic hydrocarbyl including aryl and oxyhydrocarbyl, and is preferably $C_1$-$C_4$ alkyl, especially methyl, or phenyl. $Z_2$ is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. $Z_2$ preferably will be derived from a reducing sugar in a reductive ammination reaction, most preferably $Z_2$ is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilised as well as the individual sugars listed above. These corn syrups may yield a mix of sugar components for $Z_2$. It should be understood that it is by no means intended to exclude other suitable raw materials. $Z_2$ preferably will be selected from the group consisting of $CH_2$—$(CHOH)_n$—$CH_2OH$, $CH(CH_2OH)$—$(CHOH)_{n-1}$—$CH_2OH$, $CH_2(CHOH)_2(CHOR')CHOH)CH_2)OH$, where n is an integer from 1 to 5, inclusive, and R' is H or a cyclic mono- or poly-saccharide, and alkoxylated derivatives thereof. As noted, most preferred are glycityls wherein n is 4, particularly $CH_2$—$(CHOH)_4$—$CH_2OH$.

The most preferred polyhydroxy fatty acid amide has the formula $R_8(CO)N(CH_3)CH_2(CHOH)_4CH_2OH$ wherein $R_8$ is a $C_6$-$C_{19}$ straight chain alkyl or alkenyl group. In compounds of the above formula, $R_8$—CO—N< can be, for example, cocoamide, stearamide, oleamide, lauramide, myristamide, capricamide, caprylicamide, palmitamide, tallowamide, etc.

Exemplary non-ionic surfactants suitable for use in the compositions according to the present invention include primary amines such as cocamine (available as Adagen 160D (TM) from Witco) and alkanolamines such as cocamide MEA (available as Empilan CME (TM) from Albright and Wilson), PEG-3 cocamide, cocamide DEA (available as Empilan CDE (TM) from Albright and Wilson), lauramide MEA (available as Empilan LME (TM) from Albright and Wilson), lauramide MIPA, lauramide DEA, and mixtures thereof.

Suitable amphoteric surfactants for use herein include (a) ammonium derivatives of formula [V]:

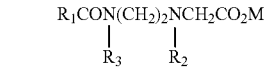

wherein $R_1$ is $C_5$-$C_{22}$ alkyl or alkenyl, $R_2$ is $CH_2CH_2OH$ or $CH_2CO_2M$, M is H, alkali metal, alkaline earth metal, ammonium or alkanolammonium and $R_3$ is $CH_2CH_2OH$ or H;

(b) aminoalkanoates of formula [VI]

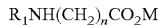

iminodialkanoates of formula [VII]

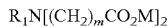

and iminopolyalkanoates of formula (VIII)

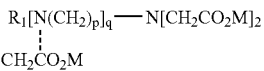

wherein n, m, p, and q are numbers from 1 to 4, and $R_1$ and M are independently selected from the groups specified above; and (c) mixtures thereof.

Suitable amphoteric surfactants of type (a) include compounds of formula (V) in which $R_1$ is $C_8H_{17}$ (especially isocapryl), $C_9H_{19}$ and $C_{11}H_{23}$ alkyl. Suitable amphoteric surfactants of type (a) are marketed under the trade name Miranol and Empigen.

In CTFA nomenclature, materials suitable for use in the present invention include cocoamphocarboxypropionate, cocoamphocarboxy propionic acid, cocoamphoacetate, cocoamphodiacetate (otherwise referred to as cocoamphocarboxyglycinate), sodium lauroamphoacetate (otherwise referred to as sodium lauroamphocarboxyglycinate). Specific commercial products include those sold under the trade names of Ampholak 7TX (sodium carboxy methyl tallow polypropyl amine), Empigen CDL60 and CDR 60 (Albright & Wilson), Miranol H2M Conc. Miranol C2M Conc. N.P., Miranol C2M Conc. O.P., Miranol C2M SF, Miranol CM Special, Miranol Ultra L32 and C32 (Rhône-Poulenc); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercotic MS-2 (Scher Chemicals).

It will be understood that a number of commercially-available amphoteric surfactants of this type are manufactured and sold in the form of electroneutral complexes with, for example, hydroxide counterions or with anionic sulfate or sulfonate surfactants, especially those of the sulfated $C_8$-$C_{18}$ alcohol, $C_8$-$C_{18}$ ethoxylated alcohol or $C_8$-$C_{18}$ acyl glyceride types. Preferred from the viewpoint of mildness and product stability, however, are compositions which are essentially free of (non-ethoxylated) sulfated alcohol surfactants. Note also that the concentrations and weight ratios of the amphoteric surfactants are based herein on the uncomplexed forms of the surfactants, any anionic surfactant counterions being considered as part of the overall anionic surfactant component content.

Examples of suitable amphoteric surfactants of type (b) include N-alkyl polytrimethylene poly-, carboxymethylamines sold under the trade names Ampholak X07 and Ampholak 7CX by Berol Nobel and also salts, especially the triethanolammonium salts and salts of N-lauryl-beta-amino propionic acid and N-lauryl-imino-dipropionic acid. Such materials are sold under the trade name Deriphat by Henkel and Mirataine by Rhône-Poulenc.

The compositions herein can also contain from about 0.1% to about 20%, more preferably from about 0.1% to about 10%, and especially from about 1% to about 8% by weight of a zwitterionic surfactant.

Water-soluble betaine surfactants suitable for inclusion in the compositions of the present invention include alkyl betaines of the formula $R_5R_6R_7N^+ (CH_2)_nCO_2M$ and amido betaines of the formula (IX)

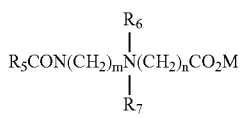

wherein $R_5$ is $C_5$-$C_{22}$ alkyl or alkenyl, $R_6$ and $R_7$ are independently $C_1$-$C_3$ alkyl, M is H, alkali metal, alkaline earth metal, ammonium or alkanolammonium, and n, m are each numbers from 1 to 4. Preferred betaines include cocoamidopropyldimethylcarboxymethyl betaine, commercially available from TH Goldschmidt under the tradename Tego betaine, and laurylamidopropyldimethylcarboxymethyl betaine, commercially available from Albright and Wilson under the tradename Empigen BR and from TH Goldschmidt under the tradename Tegobetaine L10S.

Water-soluble sultaine surfactants suitable for inclusion in the compositions of the present invention include alkylamido sultaines of the formula;

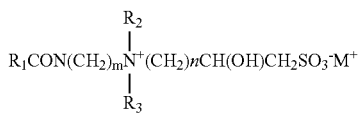

wherein $R_1$ is $C_7$ to $C_{22}$ alkyl or alkenyl, $R_2$ and $R_3$ are independently $C_1$ to $C_3$ alkyl, M is H, alkali metal, alkaline earth metal, ammonium or alkanolammonium and m and n are numbers from 1 to 4. Suitable for use herein is coco amido propylhydroxy sultaine which is commercially available under the tradename Mirataine CBS from Rhone-Poulenc.

Water-soluble amine oxide surfactants suitable for inclusion in the compositions of the present invention include alkyl amine oxide $R_5R_6R_7NO$ and amido amine oxides of the formula

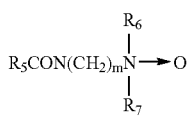

wherein $R_5$ is $C_{11}$ to $C_{22}$ alkyl or alkenyl, $R_6$ and $R_7$ are independently $C_1$ to $C_3$ alkyl, M is H, alkali metal, alkaline earth metal, ammonium or alkanolammonium and m is a number from 1 to 4. Preferred amine oxides include cocoamidopropylamine oxide, lauryl dimethyl amine oxide and myristyl dimethyl amine oxide.

Suspending Agents

The personal care compositions of the present invention optionally comprise a suspending agent. Suitable suspending agents for use herein include any of several long chain acyl derivative materials or mixtures of such materials. Included are ethylene glycol esters of fatty acids having from about 16 to about 22 carbon atoms. Preferred are the ethylene glycol stearates, both mono and distearate, but particularly the distearate containing less than about 7% of the mono stearate. Other suspending agents found useful are alkanol amides of fatty acids, having from about 16 to 22 carbon atoms, preferably from about 16 to 18 carbon atoms. Preferred alkanol amides are stearic monoethanolamide, stearic diethanolamide, stearic monoisopropanolamide and stearic monoethanolamide stearate.

Still other suitable suspending agents are alkyl ($C_{16}$-$C_{22}$) dimethyl amine oxides such as stearyl dimethyl amino oxide and trihydroxystearin commercially available under the tradename Thixcin (RTM) from Rheox. A preferred suspending agent for use herein is Thixcin (RTM) from Rheox.

The suspending agent is preferably present at a level of from about 0.1% to about 5%, preferably from about 0.1% to about 3%. The suspending agent can be utilized to assist in suspending the visible beads and/or skin benefit agents and can give pearlescence to the product. Mixtures of suspending agents are also suitable for use in the compositions of this invention.

Aqueous Carrier

The personal care compositions of the present invention optionally comprise an aqueous carrier. The level and species of the carrier are selected according to the compatibility with other components, and other desired characteristic of the product.

Carriers useful in the present invention include water and water solutions of lower alkyl alcohols. Lower alkyl alcohols useful herein are monohydric alcohols having 1 to 6 carbons, more preferably ethanol and isopropanol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 40% to about 98%, and more preferably from about 50% to about 98% water.

Skin Benefit Agents

The present compositions can optionally further comprise a skin benefit agent to provide additional benefits to the treated skin. The skin benefit agents can be contained within the visible beads of the present compositions, or can be present in the personal care compositions outside of the beads, or both. When present, skin benefit agents can be incorporated in the present compositions at levels of from about 0.0001% to about 40%, preferably from about 0.01% to about 20%, and more preferably from about 0.1% to about 10%, by weight of the composition. Suitable skin benefit agents herein include, but are not limited to, the following:

silicone oils and modifications thereof such as linear and cyclic polydimethylsiloxanes; amino, alkyl, alkylaryl, and aryl silicone oils;

fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

waxes such as carnauba, spermaceti, beeswax, lanolin, and derivatives thereof;

hydrophobic and hydrophillic plant extracts;

hydrocarbons such as liquid paraffins, petrolaum, vaseline, microcrystalline wax, ceresin, squalene, pristan, and mineral oil;

higher fatty acids such as lauric, myristic, palmitic, stearic, behenic, oleic, linoleic, linolenic, lanolic, isostearic, arachidonic and poly unsaturated fatty acids (PUFA);

higher alcohols such as lauryl, cetyl, stearyl, oleyl, behenyl, cholesterol and 2-hexydecanol alcohol;

esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

essential oils and extracts thereof such as mentha, jasmine, camphor, white cedar, bitter orange peel, ryu, turpentine, mulberry bark, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

lipids such as cholesterol, ceramides, sucrose esters, and pseudo-ceramides;

shea butter;

perfume;

vitamins, minerals, and skin nutrients such as milk, vitamin A (rentinyl propionate), vitamin B3 (niacinamide), vitamin C (sodium asocrbyl phosphate), vitamin E (tocopheryl acetate), and vitamin K; vitamin alkyl esters, including vitamin C alkyl esters; magnesium, calcium, copper, zinc, and other metallic components;

sunscreens such as octyl methoxyl cinnamate (Parsol MCX) and butyl methoxy benzoylmethane (Parsol 1789);

phospholipids;

amino acids such as asparagine, alanin, indole, glutamic acid, tyrosine, tryptamine, and salts thereof;

skin whitening compounds such as titanium dioxide;

antiaging compounds such as alpha hydroxy acids, beta hydroxy acids; and mixtures of any of the foregoing components, and the like. Preferably the skin benefit agent is selected from vegetable oils, esters, animal fats, mineral oil, petrolatum, silicone oil, or mixtures thereof, and the like. More preferably the skin benefit agent is selected from sunflower seed oil, soybean oil, castor oil, almond oil, safflower oil, sesame oil, canola oil, jojoba oil, or olive oil. A preferred skin benefit agent is sunflower seed oil.

High Molecular Weight Ester Oils

The present compositions optionally further comprise high molecular weight ester oils. The high molecular weight ester oils useful herein are typically those which are water insoluble, have a molecular weight of at least about 500, preferably at least about 800, and are in liquid form at 25° C. Useful high molecular weight ester oils herein include pentaethytritol ester oils, trimethylol ester oils, poly alpha-olefin oils, citrate ester oils, glyceryl ester oils, and mixtures thereof. The high molecular weight ester oils herein can provide conditioning benefits such as moisturized feel and smooth feel to the skin, yet not leave the skin feeling greasy. When present, the high molecular weight ester oil is preferably present at a level from about 0.01% to about 5%, preferably from about 0.01% to about 3% and especially from about 0.01% to about 2%, by weight of the composition.

Pentaerythritol ester oils useful herein are those having the following formula:

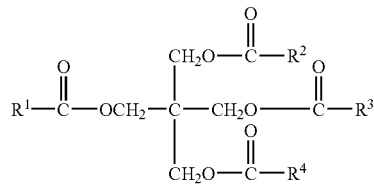

wherein $R^1$, $R^2$, $R^3$, and $R^4$, independently, are branched, straight, saturated, or unsaturated alkyl, aryl, and alkylaryl groups having from 1 to about 30 carbons. Preferably, $R^1$, $R^2$, $R^3$, and $R^4$, independently, are branched, straight, saturated, or unsaturated alkyl groups having from about 8 to about 22 carbons. More preferably, $R^1$, $R^2$, $R^3$ and $R^4$ are defined so that the molecular weight of the compound is from about 800 to about 1200.

Trimethylol ester oils useful herein are those having the following formula:

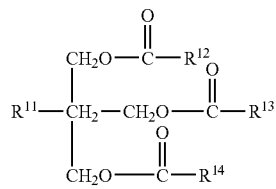

wherein $R^{11}$ is an alkyl group having from 1 to about 30 carbons, and $R^{12}$, $R^{13}$, and $R^{14}$, independently, are branched, straight, saturated, or unsaturated alkyl, aryl, and alkylaryl groups having from 1 to about 30 carbons. Preferably, $R^{11}$ is ethyl and $R^{12}$, $R^{13}$, and $R^{14}$, independently, are branched, straight, saturated, or unsaturated alkyl groups having from 8 to about 22 carbons. More preferably, $R^{11}$, $R^{12}$, $R^{13}$ and $R^{14}$ are defined so that the molecular weight of the compound is from about 800 to about 1200.

Poly alpha-olefin oils useful herein are those having the following formula and having a viscosity of from about 1 to about 35,000 cst, a molecular weight of from about 200 to about 60,000, and a polydispersity of no more than about 3;

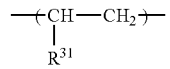

wherein $R^{31}$ is an alkyl having from about 4 to 14 carbons, preferably 4 to 10 carbons. Poly alpha-olefin oils having a molecular weight of at least about 800 are useful herein. Such high molecular weight poly alpha-olefin oils are believed to provide long lasting moisturized feel to the hair. Poly alpha-olefin oils having a molecular weight of less than about 800 are useful herein. Such low molecular weight poly alpha-olefin oils are believed to provide a smooth, light, clean feel to the hair.

Citrate ester oils useful herein are those having a molecular weight of at least about 500 having the following formula:

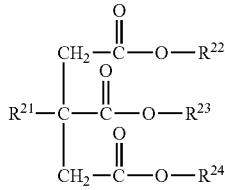

wherein $R^{21}$ is OH or $CH_3COO$, and $R^{22}$, $R^{23}$, and $R^{24}$, independently, are branched, straight, saturated, or unsaturated alkyl, aryl, and alkylaryl groups having from 1 to about 30 carbons. Preferably, $R^{21}$ is OH, and $R^{22}$, $R^{23}$, and $R^{24}$, independently, are branched, straight, saturated, or unsaturated alkyl, aryl, and alkylaryl groups having from 8 to about 22 carbons. More preferably, $R^{21}$, $R^{22}$, $R^{23}$ and $R^{24}$ are defined so that the molecular weight of the compound is at least about 800.

Glyceryl ester oils useful herein are those having a molecular weight of at least about 500 and having the following formula:

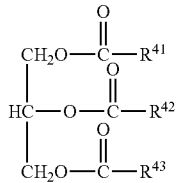

wherein $R^{41}$, $R^{42}$, and $R^{43}$, independently, are branched, straight, saturated, or unsaturated alkyl, aryl, and alkylaryl groups having from 1 to about 30 carbons. Preferably, $R^{41}$, $R^{42}$, and $R^{43}$, independently, are branched, straight, saturated, or unsaturated alkyl, aryl, and alkylaryl groups having from 8 to about 22 carbons. More preferably, $R^{41}$, $R^{42}$, and $R^{43}$ are defined so that the molecular weight of the compound is at least about 800.

Particularly useful pentaerythritol ester oils and trimethylol ester oils herein include pentaerythritol tetraisostearate, pentaerythritol tetraoleate, trimethylolpropane triisostearate, trimethylolpropane trioleate, and mixtures thereof. Such compounds are available from Kokyo Alcohol with tradenames KAKPTI, KAKTTI, and Shin-nihon Rika with tradenames PTO, ENUJERUBU TP3SO.

Particularly useful poly alpha-olefin oils herein include polydecenes with tradenames PURESYN 6 having a number average molecular weight of about 500 and PURESYN 100 having a number average molecular weight of about 3000 and PURESYN 300 having a number average molecular weight of about 6000 available from Mobil Chemical Co.

Particularly useful citrate ester oils herein include triisocetyl citrate with tradename CITMOL 316 available from Bernel, triisostearyl citrate with tradename PELEMOL TISC available from Phoenix, and trioctyldodecyl citrate with tradename CITMOL 320 available from Bernel.

Particularly useful glyceryl ester oils herein include triisostearin with tradename SUN ESPOL G-318 available from Taiyo Kagaku, triolein with tradename CITHROL GTO available from Croda Surfactants Ltd., trilinolein with tradename EFADERMA-F available from Vevy, or tradename EFA-GLYCERIDES from Brooks.

Humectant

The compositions of the present invention can optionally further comprise a humectant. The humectants herein are selected from the group consisting of polyhydric alcohols, water soluble alkoxylated nonionic polymers, and mixtures thereof. The humectants herein are preferably used at levels by weight of the composition of from about 0.1% to about 20%, more preferably from about 0.5% to about 5%.

Polyhydric alcohols useful herein include glycerin, sorbitol, propylene glycol, butylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sultate, sodium hyaluronate, sodium adenosin phosphate, sodium lactate, pyrrolidone carbonate, glucosamine, cyclodextrin, and mixtures thereof.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

Commercially available humectants herein include: glycerin with tradenames STAR and SUPEROL available from The Procter & Gamble Company, CRODEROL GA7000 available from Croda Universal Ltd., PRECERIN series available from Unichema, and a same tradename as the chemical name available from NOF; propylene glycol with tradename LEXOL PG-865/855 available from Inolex, 1,2-PROPYLENE GLYCOL USP available from BASF; sorbitol with tradenames LIPONIC series available from Lipo, SORBO, ALEX, A-625, and A-641 available from ICI, and UNISWEET 70, UNISWEET CONC available from UPI; dipropylene glycol with the same tradename available from BASF; diglycerin with tradename DIGLYCEROL available from Solvay GmbH; xylitol with the same tradename available from Kyowa and Eizai; maltitol with tradename MALBIT available from Hayashibara, sodium chondroitin sulfate with the same tradename available from Freeman and Bioiberica, and with tradename ATOMERGIC SODIUM CHONDROITIN SULFATE available from Atomergic Chemetals; sodium hyaluronate with tradenames ACTIMOIST available from Active Organics, AVIAN SODIUM HYALURONATE series available from Intergen, HYALURONIC ACID Na available from Ichimaru Pharcos; sodium adenosin phophate with the same tradename available from Asahikasei, Kyowa, and Daiichi Seiyaku; sodium lactate with the same tradename available from Merck, Wako, and Showa Kako, cyclodextrin with tradenames CAVITRON available from American Maize, RHODOCAP series available from Rhone-Poulenc, and DEXPEARL available from Tomen; and polyethylene glycols with the tradename CARBOWAX series available from Union Carbide.

Adjunct Ingredients

The present compositions can further comprise cosmetically-acceptable adjunct ingredients such as perfume, chelants (e.g. disodium EDTA), preservatives (e.g. Kathon CG, sodium benzoate), visual aids (e.g. oxidized polyethylene), pH control agents (e.g. citric acid), UV absorbers, optical brighteners, and the like.

The pH of the present compositions is preferably from about 3 to about 10, more preferably from about 5 to about 9, especially from about 5 to about 8 and most preferably from about 5 to 7.

The compositions of the present invention can be used for a variety of skin and hair care applications such as shower gels, bar soaps, body washes, hair shampoos, and the like. In one embodiment, the present composition is a liquid body wash composition.

The compositions of the present invention may be applied to skin and/or hair with the hand or preferably with a personal cleansing implement such as a puff. Suitable personal cleansing implements for use with the compositions of the present invention include those disclosed in the following patent documents: U.S. Pat. No. 5,144,744; U.S. Pat. No. 3,343,196; WO 95/26671; WO 95/00116; and WO 95/26670.

The compositions of the present invention can be transparent, translucent, or opaque personal care compositions.

The present compositions will preferably have a viscosity of from about 1,000 to about 400,000 centipoise, more preferably from about 1,000 to about 100,000 centipoise, more preferably from about 1,000 to less than about 40,000 centipoise, more preferably from about 1,000 to about 35,000 centipoise, more preferably from about 1,000 to about 30,000 centipoise, and more preferably from about 1,000 to about 20,000 centipoise. The viscosity of the personal care composition is measured with a Brookfield RVT DV-II Viscometer (CP52 cone spindle, 1 RPM, at 25° C.).

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified.

EXAMPLES

The following are non-limiting examples of liquid body wash compositions according to the present invention. The amounts below are provided as weight percent.

| Ingredient | EXAMPLES I | EXAMPLES II |
|---|---|---|
| Ammonium Laureth-3 Sulfate | 10 | 10 |
| Cocamidopropyl Betaine | 1.5 | 1.5 |
| Sodium Lauroamphoacetate | 1 | 1 |
| Perfume | 1 | 1 |
| Cationic Polymer (N-Hance 3196) [a] | 0.35 | 0.35 |
| Trihydroxystearin [b] | 0.3 | 0.3 |
| Sodium Benzoate | 0.25 | 0.25 |
| Glycerin | 0.2 | 0.2 |
| Citric Acid, anhydrous | 0.15 | 0.15 |
| Polyquaternium-10 | 0.1 | 0.1 |
| Disodium EDTA | 0.1 | 0.1 |
| Titanium Dioxide 328 | 0.1 | 0.1 |
| Oxidized Polyethylene | 1 | 1 |
| Polyox WSR N-3000 [c] | 0.05 | 0.05 |
| Kathon CG [d] | 0.0005 | 0.0005 |
| Unispheres AGE-527 [e] | 0.05 | 0.05 |
| Mulberry Bark Extract | 0.0005 | 0.0005 |
| Sodium Ascorbyl Phosphate [f] | 0.0005 | 0.0005 |
| DL-Alpha Tocopheryl Acetate [g] | 0.0005 | 0.0005 |
| Rentinyl Proprionate [h] | 0.0005 | 0.0005 |
| Niacinamide, USP [i] | 0.0005 | 0.0005 |
| Puresyn 101LT [j] | — | 1 |
| Water | Balance | Balance |

[a] Guar Hydroxypropyl Trimonium Chloride available from Aqulon.
[b] Thixcin available from Rheox.
[c] PEG-14M available from Dow Chemical Co.
[d] Preservative available from Rohm & Haas.
[e] Visible beads comprising lactose, cellulose, hydroxypropyl methylcellulose, chromium hydroxide green, and tocopheryl acetate; available from Induchem.
[f] Vitamin C.
[g] Vitamin E.
[h] Vitamin A.
[i] Vitamin B3.
[j] Polydecene available from ExxonMobil Chemical Co.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
    (a) visible beads;
    (b) cationic polymer;
    (c) surfactant selected from the group consisting of anionic surfactant, nonionic surfactant, amphoteric surfactant, zwitterionic surfactant and mixtures thereof; and
    (d) high molecular weight ester oil.

2. The personal care composition of claim 1, wherein said high molecular weight molecular weight ester oil is a poly alpha-olefin.

3. The personal care composition of claim 2, wherein said poly alpha-olefin is a polydecene.

4. The personal care composition of claim 1, wherein said visible beads further comprise an encompassed material.

5. The personal care composition of claim 4, wherein said encompassed material is a skin benefit agent.

6. The personal care composition of claim 5, wherein said skin benefit agent is tocopheryl acetate.

7. The personal care composition of claim 1, wherein said visible bead further comprises a pigment.

8. The personal care composition of claim 1, wherein said personal care composition further comprises a suspending agent.

9. The personal care composition of claim 8, wherein said suspending agent is trihydroxystearin.

10. The personal care composition of claim 1, wherein said personal care composition further comprises a skin benefit agent.

11. The personal care composition of claim 1, wherein said personal care composition comprises from about 2% to about 40%, by weight of said composition, of said surfactant.

12. The personal care composition of claim 1, wherein said personal care composition further comprises from about 20% to about 99%, by weight of said composition, of aqueous carrier.

13. The personal care composition of claim 1, wherein said personal care composition is a liquid body wash composition.

14. A method of cleansing skin comprising the step of contacting said skin with a personal care composition according to claim 1.

15. The personal care composition of claim 11, wherein said personal care composition comprises from about 5% to about 20%, by weight of said personal care composition, of said surfactant.

* * * * *